United States Patent [19]
Lavigne et al.

[11] Patent Number: 5,533,514
[45] Date of Patent: Jul. 9, 1996

[54] ALGOMETRY MANAGEMENT SYSTEM

[75] Inventors: Gilles Lavigne, Ville Mont-Royal; Léo TenBokum, Montréal, both of Canada

[73] Assignee: Université de Montréal, Montréal, Canada

[21] Appl. No.: 437,701

[22] Filed: May 9, 1995

[51] Int. Cl.$^6$ .................................................. A61B 3/00
[52] U.S. Cl. ........................ 128/744; 128/740; 128/741
[58] Field of Search ................................. 128/744, 741, 128/740

[56] References Cited

U.S. PATENT DOCUMENTS

| | | | |
|---|---|---|---|
| 2,704,539 | 3/1955 | Fisher | 128/744 |
| 4,387,723 | 6/1983 | Atlee et al. | 128/734 |
| 4,543,957 | 10/1985 | Friedman et al. | 128/630 |
| 4,570,640 | 2/1986 | Barsa | 128/741 |
| 4,641,661 | 2/1987 | Kalarickal | 128/744 |
| 4,711,248 | 12/1987 | Steuer et al. | 128/748 |
| 4,844,091 | 7/1989 | Bellak | 128/744 |
| 5,022,407 | 6/1991 | Horch et al. | 128/744 |
| 5,220,921 | 6/1993 | Ferris et al. | 128/744 |
| 5,228,443 | 7/1993 | Tatar | 128/653.2 |
| 5,237,501 | 8/1993 | Gusakov | 364/413.01 |
| 5,381,805 | 1/1995 | Tuckett et al. | 128/744 |
| 5,381,806 | 1/1995 | Weinstein et al. | 128/744 |

OTHER PUBLICATIONS

"The Management of Pain" Bonica, J. J., Lea & Feliger Linchon, 2nd Edition 1990, p. 582.
"Quantification of Tenderness by Palpation and Use of Pressure Algometers" Jensen, K. Advances in Pain Research and Therapy, 1990, vol. 17, pp. 165 and 170.
"TSA 2001–The new Thermal Sensory Analyzer" Medoc Ltd. Advanced Medical Systems 1992, pp. 1–4.
"Thermotest", Somedic Sales AB, pp. 1–2.
"Algometer—For determination of pressure and pinch pain", Somedic Sales AB, pp. 1–2.
"Symtrack—The electronic diary card", Autenta AB, pp. 1–2.
"Pain and Soft Tissue Pathology Instrument", Pain Diagnostics & Thermography Bulletin 8401 pp. 1–4.

*Primary Examiner*—Angela D. Sykes
*Assistant Examiner*—Stephen D. Huang
*Attorney, Agent, or Firm*—Darby & Darby

[57] ABSTRACT

In the algometry management method and system, a computer apparatus is used to select points of a patient's body on which pain sensitivity pressure measurements have to be made, to determine a sequence of these selected points, and to indicate the selected points one by one to an operator according to the sequence. A pressure algometer is used by the operator to apply pressure to each point of the sequence indicated and to measure the pressure being applied when a patient's threshold of pain is reached, this pressure measurement constituting a pain sensitivity pressure measurement. The computer apparatus also receives the pain sensitivity pressure measurement from the algometer for each point of the sequence, and stores the received pain sensitivity pressure measurements in a file associated to the patient. The method and system also ask to the patient a subjective indication of the intensity of pain and degree of discomfort he felt upon application of pressure to each point of the patient's body. A visual analog scale unit is provided to allow the patient to give this subjective indication of the intensity of pain and degree of discomfort he felt.

22 Claims, 4 Drawing Sheets

ALGOMETRY MANAGEMENT SYSTEM

BACKGROUND OF THE INVENTION

1. Field of the Invention

The present invention relates to an algometry management method and system adapted for reducing the time required by a physician to evaluate pain.

2. Brief Description of the Prior Art

Pain is a subjective, complex phenomenon consisting of (a) a sensorial perception sometimes revealing a potential or real tissular lesion, and (b) the affective response provoked by this sensorial perception. As pain sensation is also psychic, objective evaluation thereof is difficult.

Presently, two main types of pain evaluation are currently used during clinical examination of patients: evaluation of the sensitivity of the affected tissues to pain, and evaluation of the "clinical pain".

Evaluation of pain sensitivity is generally performed by means of palpation of skin or underlying tissues (for example muscles), or by means of other more or less reliable methods. Both the response to manual palpation and evaluation of pain sensitivity from this response are complex and often unreliable.

"Clinical pain" is usually evaluated from a verbal report of the patient; these verbal reports are generally unreliable since they depend on the patient's "pain memory" and since chronic pain may widely vary within a same day and from one day to the other. Those of ordinary skill in the art know that retrospective symptom data are notoriously inaccurate.

OBJECTS OF THE INVENTION

An object of the present invention is therefore to provide an algometry management method and system for managing, in particular but not exclusively objective and subjective measurement of the intensity of pain and degree of discomfort felt by a patient, to thereby improve the accuracy of the collected data.

SUMMARY OF THE INVENTION

More specifically, in accordance with the present invention, there is provided an algometry management method, comprising the steps of:

- selecting points of a patient's body on which pain sensitivity measurements have to be made by an operator;
- determining a sequence of the selected points;
- indicating to the operator, according to the sequence, each selected point of the patient's body on which a pain sensitivity measurement has to be made;
- receiving the pain sensitivity measurement made by the operator on each point of the sequence indicated by the indicating means;
- storing the received pain sensitivity measurement of each point of the sequence in a file associated to the patient.

The present invention also relates to an algometry management system, comprising:

- means for selecting points of a patient's body on which pain sensitivity measurements have to be made by an operator;
- means for determining a sequence of the selected points;
- means for indicating to the operator, according to the sequence, each selected point of the patient's body on which a pain sensitivity measurement has to be made;
- means for receiving the pain sensitivity measurement made by the operator on each point of the sequence indicated by the indicating means;
- means for storing the received pain sensitivity measurement of each point of the sequence in a file associated to the patient.

In accordance with preferred embodiments of the subject invention:

- selection of points of the patient's body is carried out by displaying at least one representation of the patient's body, and marking the selected points on this representation;
- bilateral points can be selected and marked on the representation(s) of the patient's body;
- advantageously, the sequence of selected points is determined randomly;
- each point of the patient's body is indicated one by one, according to the sequence, on the representation(s) of the patient's body;
- pressure is applied to each point of the sequence by means of a pressure algometer, the pressure applied to each point of the patient's body is measured by the pressure algometer, and that pressure algometer holds a measurement of the pressure being applied to the point of the patient's body when the patient indicates that a threshold of pain has been reached by depressing a push-button connected to the algometer; and
- a subjective indication of the intensity of pain and degree of discomfort the patient felt upon application of the pressure is asked to the patient who answers by displacing a cursor means along a visual analog scale to produce the subjective indication of the intensity of pain or degree of discomfort, the position of the cursor means along the visual analog scale being converted to a pain intensity representative signal.

The objects, advantages and other features of the present invention will become more apparent upon reading of the following non restrictive description of a preferred embodiment thereof, given by way of example only with reference to the accompanying drawings.

DETAILED DESCRIPTION OF THE PREFERRED EMBODIMENT

Figure 1:
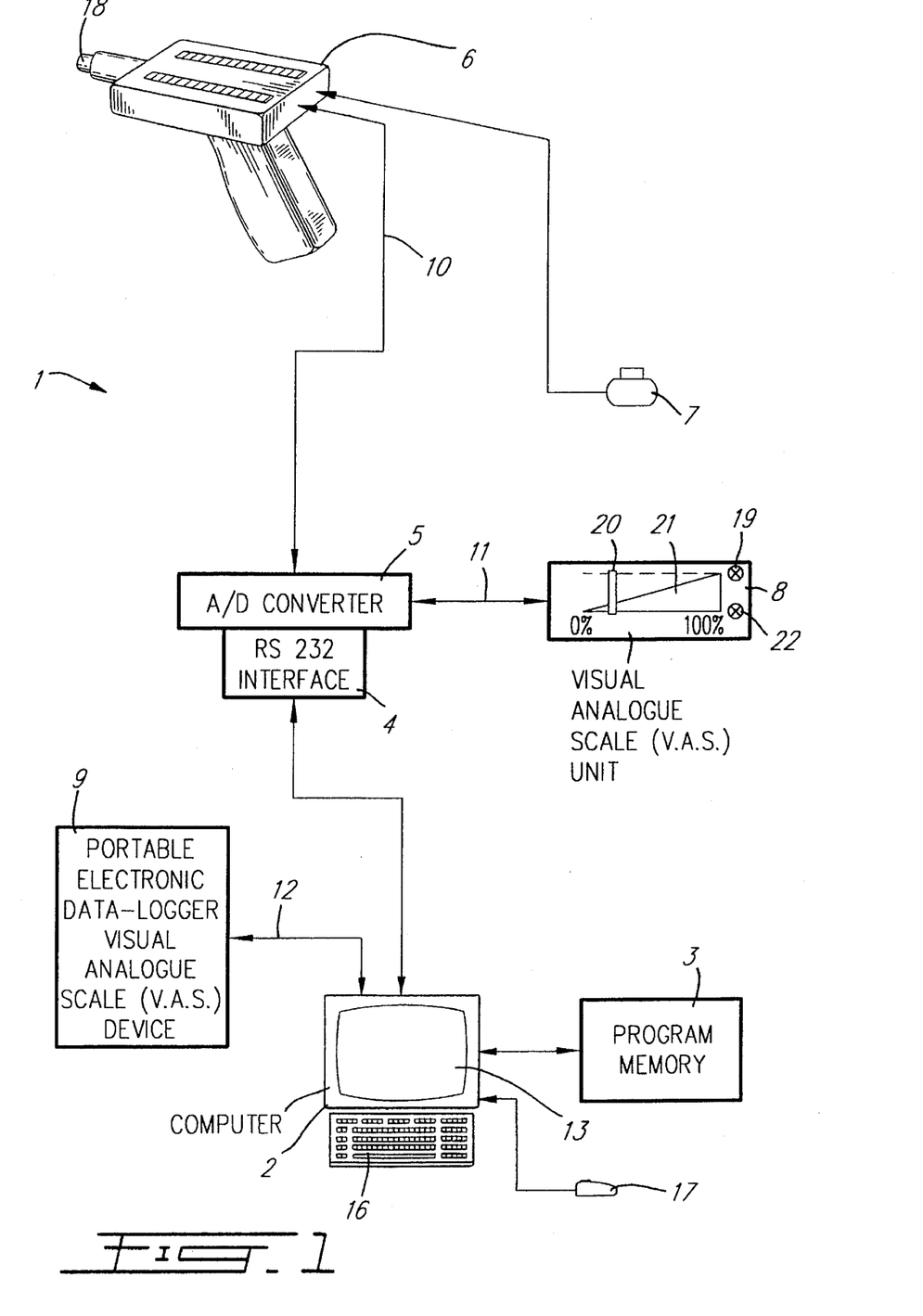
FIG. 1 is a schematic block diagram of an algometry management system in accordance with the present invention.
Figure 2A:
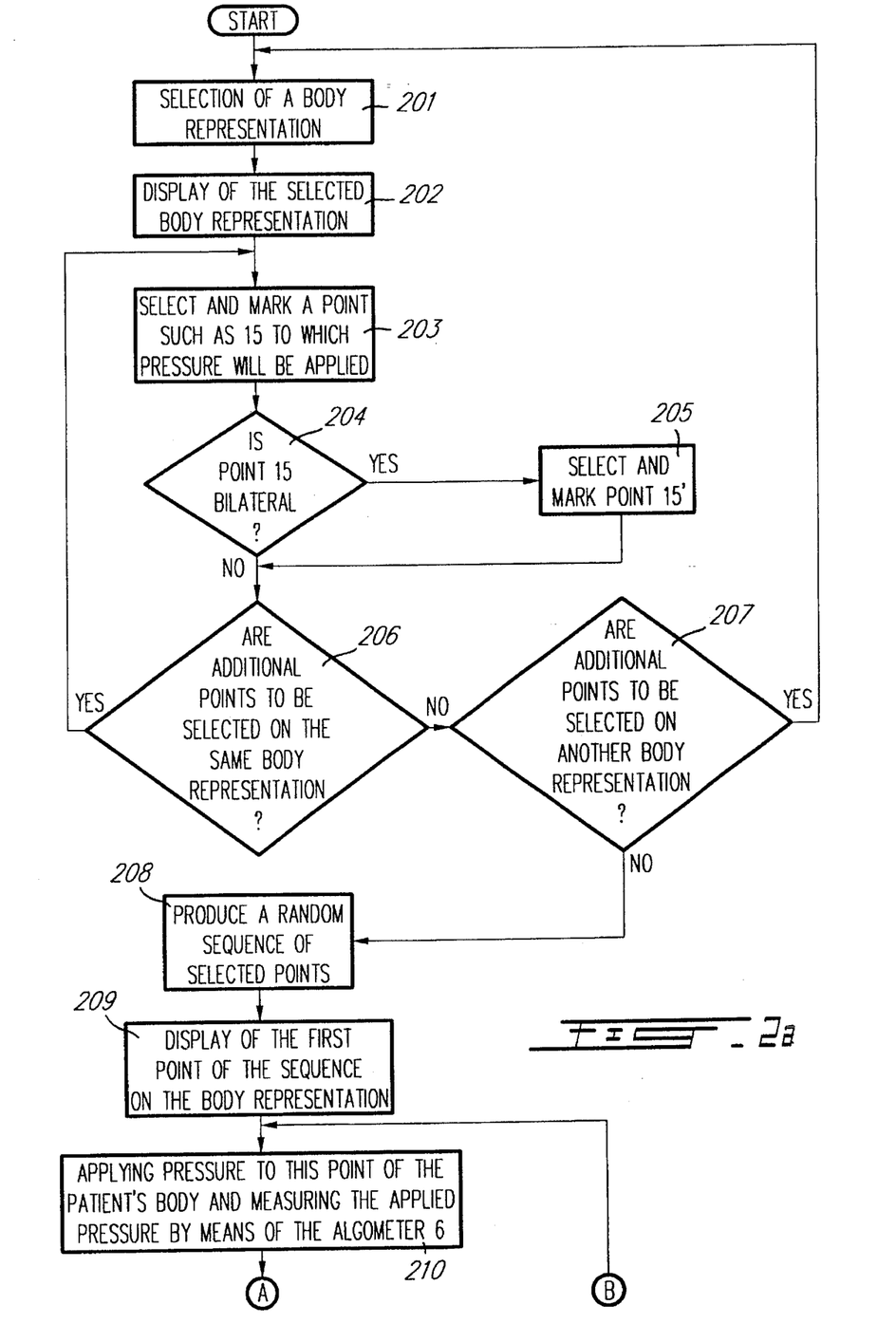
FIG. 2a is a first portion of a flow chart illustrating operation of the algometry management system of FIG. 1.
Figure 2B:
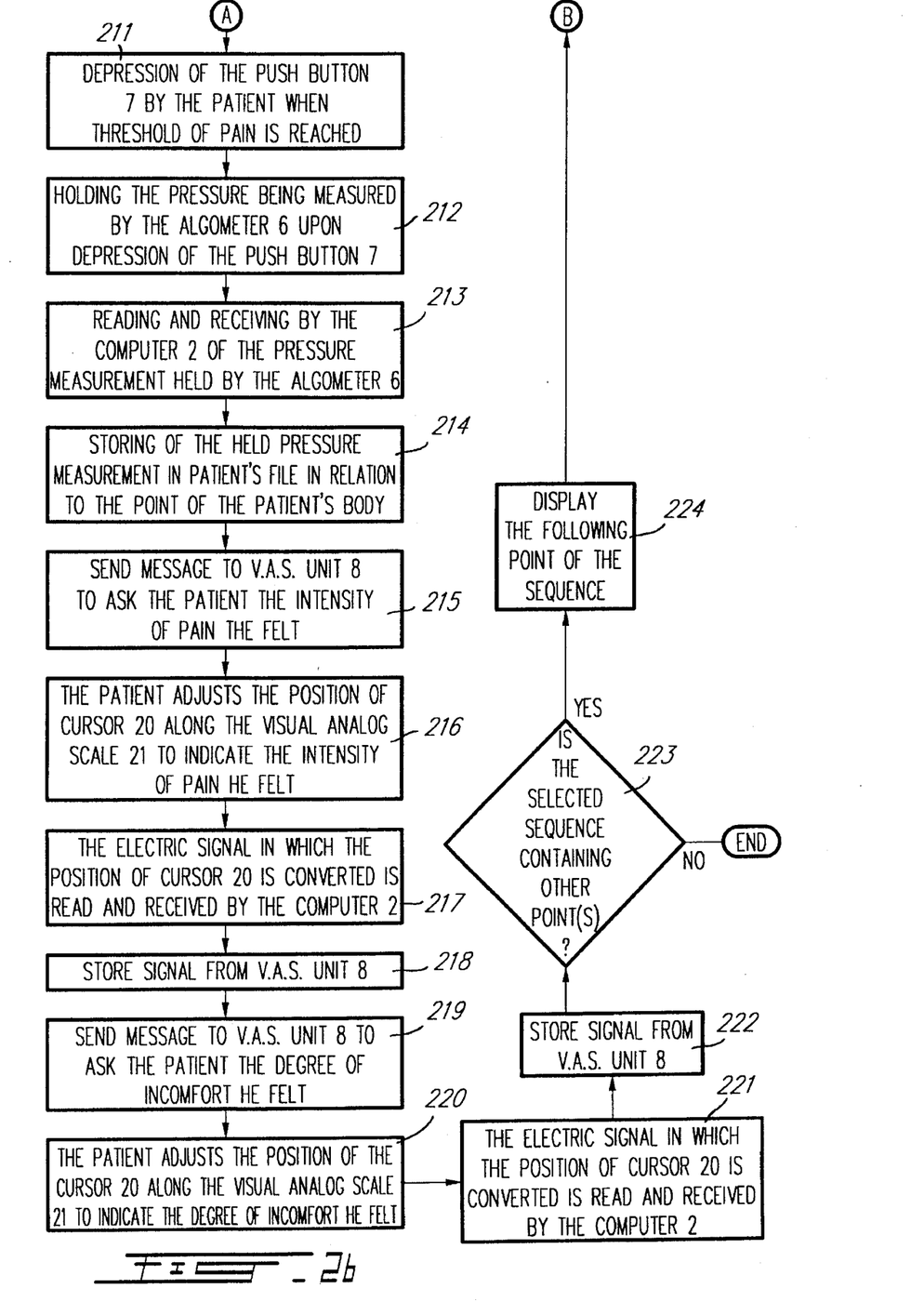
FIG. 2b is a second portion of the flow chart illustrating operation of the algometry management system of FIG. 1.

The algometry management system in accordance with the present invention is generally identified by the reference 1 in FIG. 1 of the appended drawings.

As illustrated in FIG. 1, the algometry management system 1 comprises:

a computer 2 provided with a program memory 3, a display screen 13, a keyboard 16 and a mouse 17;

an analog-to-digital (A/D) converter 5 associated to a RS 232 interface 4 establishing bidirectional communication between the A/D converter 5 and the computer 2;

an algometer 6 including a pressure-applying tip 18 and being connected to the A/D converter 5 through a bidirectional line 10, the algometer 6 being preferably the algometer described and claimed in copending patent application No. , filed on *;

a patient-operated stop push-button 7 connected to the algometer 6;

a visual analogue scale (V.A.S.) unit 8 connected to the A/D converter 5 through a bidirectional line 11, and comprising a cursor 20, a visual analogue scale 21, light-emitting diodes (LED's) 19 and 22 and a circuit for producing an analog electric signal having an amplitude corresponding to the position of the cursor 20 along the visual analog scale 21; and a portable electronic data-logger visual analogue scale device 9 connectable to a serial port (not shown) of the computer 2 through a bidirectional line 12.

Operation of the algometry management system 1 will now be described with reference to FIGS. 1, 2a, 2b and 3 of the appended drawings.

Step 201

Different human body representations are available for display on the screen 13 (FIG. 1) of the computer 2, such as front, back and side representations. In a first step (step 201) the operator, a physician or other medical practitioner, selects the human body representation corresponding to the region of the patient's body in which pain sensitivity measurements have to be made to evaluate sensitivity of the patient to pain in the region of interest of the patient's body.

Step 202

Figure 3:
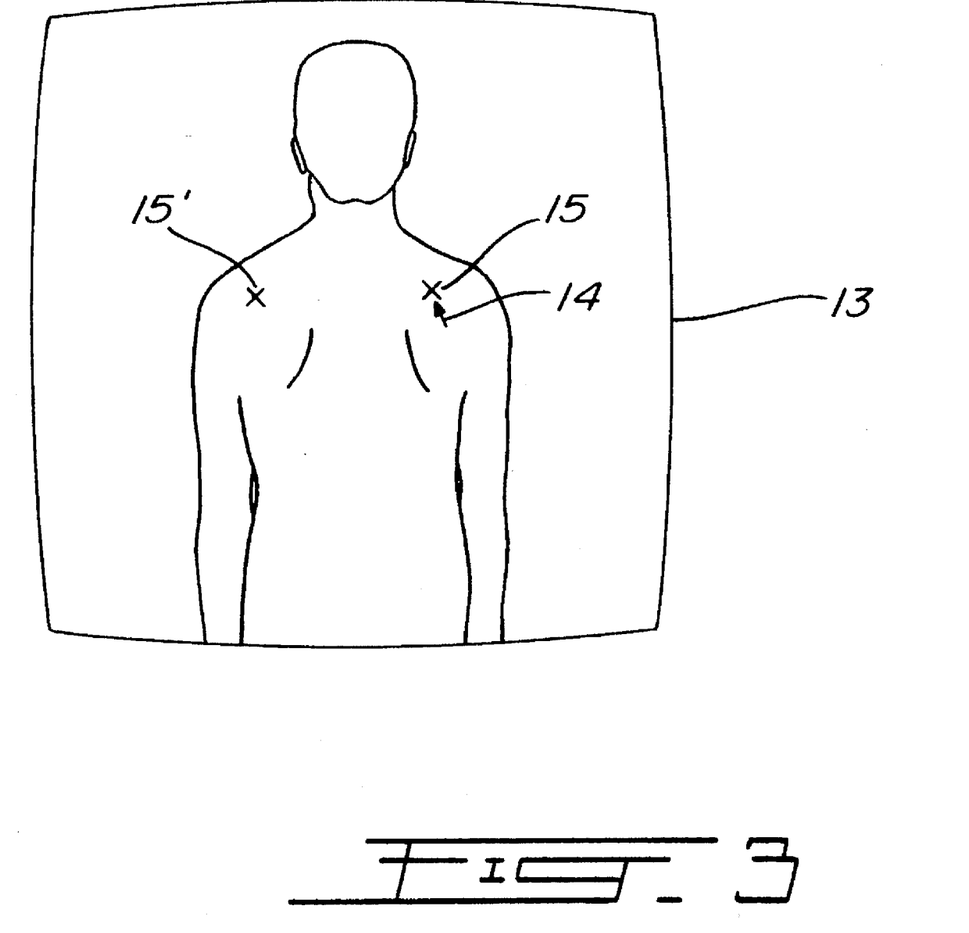
FIG. 3 is an example of body representation displayed by the algometry management system according to the invention.

The selected body representation is then displayed on the screen 13. In the example of FIG. 3, the back of the human body is displayed on the screen 13.

Step 203

By means of a cursor 14 (FIG. 3) displaceable through keys of the keyboard 16 or the mouse 17, a point 15 on which at least one pain sensitivity measurement will be made is selected and marked on the body representation (see for example the "x" mark associated to point 15.

Step 204

In this step, the operator indicates through the keyboard 16 or the mouse 17 whether the selected point such as 15 is bilateral.

Step 205

If the selected point such as 15 is bilateral, the corresponding point such as 15' on the other side of the human body is automatically selected and marked (see the "x" mark of FIG. 3 associated to point 15').

Step 206

When additional points have to be selected on the same body representation, the program is operated to return to step 203. Otherwise, the program goes to step 207.

Step 207

When additional points have to be selected on another body representation, the program is operated to return to step 201. Otherwise, the program goes to step 208.

Those of ordinary skill in the art will appreciate that the points of the body are selected in function of the diagnosis to be established.

Step 208

Pressure is applied to the selected points according to a sequence. Any given sequence can be determined by the operator through the keyboard 16 and/or the mouse 17.

Advantageously, the computer 2 is programmed to produce a random sequence of the selected points.

The sequence can be repetitive or not. Also, a same point can be repeated in the sequence.

The advantage of producing a random sequence is that the sequence changes at from one examination to the other whereby the influence from the outside, for example bias induced by the operator (physician or other medical practitioner) and/or the patient is if not completely eliminated, greatly reduced. Objectivity of the diagnosis is thereby improved. Also, two or three additional points are selected for each patient to make the diagnosis personal.

Step 209

After the sequence of points has been determined, the computer 2 displays on the screen 13 the different points of the sequence one by one. In step 209, the first point of the sequence is indicated on the body representation displayed on the screen 13.

Step 210

The operator then uses the algometer 6 for applying pressure by means of the pressure-applying tip 18 to the point of the patient's body corresponding to the point indicated on the body representation displayed on the screen 13, the algometer measuring the applied pressure.

Step 211

As pressure is applied to the point of interest of the patient's body through the tip 18 of the algometer 6, the patient is feeling pain. The patient is holding the stop push-button 7 and he is instructed to signal that the pain threshold has been reached by depressing that stop push-button 7, the pressure at this moment being the pressure-pain threshold and therefore constituting a pain sensitivity measurement.

Step 212

Depression of the stop push-button 7 causes the algometer 6 to hold the pressure being measured at this moment.

Step 213

The computer 2 is then operated to read and receive the pressure measurement held by the algometer 6. Then, the computer 2 sends a "read" message to the A/D converter 5 through the RS 232 interface 4. The analog pressure measurement signal held by the algometer 6 upon depression of the stop push-button 7 by the patient is then converted to a pressure representative digital signal by the A/D converter 5, and transmitted to and received by the computer 2 through the RS 232 interface 4. This constitutes an objective measurement of the sensitivity of the patient's body to pain.

Step 214

The computer 2 then stores automatically the pressure measurement received from the algometer 6 in the file of the patient being investigated, in relation to the point of the patient's body to which pressure has been applied.

Step 215

The computer 2 sends a message to the V.A.S. unit 8 through the RS 232 interface 4 and the A/D converter 5 to light a first light-emitting diode (LED) 19 and thereby ask the patient the intensity of pain he felt upon application of pressure to the first point of the sequence.

Step 216

The patient then slides the cursor 20 of the V.A.S. unit 8 along the visual analogue scale 21 to a position corresponding on the scale 21 to the intensity of pain he felt, keeping in mind that the intensity is 0% at the left end of the scale 21 and 100% at the right end thereof.

Step 217

The V.A.S. unit 8 contains a circuit to produce an analog electric signal whose amplitude corresponds to the position of the cursor 20 along the visual analog scale 21. This electric signal is converted to a digital signal by the A/D converter 5, and transmitted to the computer 2 through the RS 232 interface 4. This electric signal is thereby read and received by the computer 2 and constitutes a subjective indication of the intensity of pain felt by the patient.

Step 218

The computer 2 then stores automatically the signal from the V.A.S. unit 8 in the file of the patient being investigated, in relation to the point of the patient's body to which pressure has been applied.

Step 219

The computer 2 then sends a second message to the V.A.S. unit 8 through the RS 232 interface 4 and the A/D converter 5 to light a second light-emitting diode (LED) 22 and thereby ask the patient the degree of discomfort he felt upon application of pressure to the point of interest.

Step 220

The patient then slides the cursor 20 of the V.A.S. unit 8 along the visual analogue scale 21 to a position corresponding on the scale 21 to the degree of discomfort he felt, keeping in mind that the degree of discomfort is 0% at the left end of the scale 21 and 100% at the right end thereof.

Step 221

The electric analog signal produced by the V.A.S. unit 8 and having an amplitude corresponding to the position of the cursor 20 along the visual analog scale 21 is converted to a digital signal by the A/D converter 5, and transmitted to the computer 2 through the RS 232 interface 4. This electric signal is thereby read and received by the computer 2 and constitutes a subjective indication of the degree of discomfort felt by the patient upon application of pressure.

Step 222

The computer 2 then stores automatically the signal from the V.A.S. unit 8 in the file of the patient being investigated, in relation to the point of the patient's body to which pressure has been applied. Step 223

If the sequence is not completed and contains other points of the patient's body to which pressure has to be applied through the pressure-applying tip 18 of the algometer 6, the program goes to step 224.

If the sequence is completed, the procedure is terminated.

Step 224

The following point of the sequence is displayed and the program returns to step 210.

The computer 2 is also connectable to a portable electronic data-logger visual analogue scale device 9 through a bidirectional line 12. The data-logger device is preferable of the type described and illustrated in copending patent application No. * filed on *.

The portable electronic data-logger visual analogue scale device 9 comprises an RS 232 interface (not shown). The program is loaded by the computer 2 in the data-logger device 9 through the RS 232 interface and the bidirectional line 12. In the same manner, the data collected by means of the portable electronic data-logger visual analogue scale device 9 are transferred to the computer 2 also through the RS 32 interface and the bidirectional line 12.

The computer program stored in memory 3 is further adapted to carry out many other functions such as:

(a) Compilation of the collected data (pain measurements at the different points of the sequence, subjective pain intensity and degree of discomfort, time, points of application of pressure, etc.);

(b) Calculation of statistic values such as the average, the variance and the standard deviation of data;

(c) Calculations performed on these statistic values for hypothesis test purposes;

(d) Collecting the data in view of recording and storing the objective and subjective pain components (values);

(e) Comparison of the results at certain time intervals;

(f) Management of the files of the patients (name, age, sex, address, telephone, date and reason of examination, illness history, etc.); and (g) Printing of the results of the evaluation. As can be appreciated by those of ordinary skill in the art, the algometry management system according to the invention greatly reduces the time required by a physician to evaluate pain.

Although the present invention has been described hereinabove by way of a preferred embodiment thereof, this embodiment can be modified at will, within the scope of the appended claims, without departing from the spirit and nature of the subject invention.

What is claimed is:

1. An algometry management system, comprising:

means for selecting points of a patient's body on which pain sensitivity measurements are to be made by an operator;

means for determining a sequence of the selected points;

means for indicating to the operator, according to said sequence, each selected point of the patient's body on which a pain sensitivity measurement is to be made;

means for receiving the pain sensitivity measurement made by the operator on each point of said sequence indicated by said indicating means;

means for storing the received pain sensitivity measurement of each point of said sequence in a file associated with the patient;

means for asking the patient for a subjective indication of at least one sensation felt during each pain sensitivity measure; and patient-operated means for producing a signal representative of said subjective indication, wherein said receiving means comprises means for receiving said subjective indication representative signal and said storing means comprises means for storing said subjective indication representative signal in the file of the patient, said patient-operated means including;

(a) a visual analog scale;

(b) cursor means displaceable along the visual analog scale to produce said subjective indication; and (c) means for converting a resulting position of the cursor means along the visual analog scale into said subjective indication representative signal.

2. An algometry management system as recited in claim 1, wherein said means for selecting points of a patient's body comprises:

means for displaying at least one representation of the patient's body; and means for marking on said at least one representation of the patient's body the selected points.

3. An algometry management system as recited in claim 2, wherein said means for selecting points of a patient's body comprises means for selecting bilateral points and for marking said bilateral points on said at least one representation of the patient's body.

4. An algometry management system as recited in claim 1, wherein said means for determining a sequence of the selected points comprises means for producing a random sequence of the selected points.

5. An algometry management system as recited in claim 2, wherein said means for indicating to the operator, according to said sequence, each selected point of the patient's body comprises means for indicating one by one the points of the sequence on said at least one representation of the patient's body.

6. An algometry management system as recited in claim 1, further comprising a pressure algometer used by the operator for applying pressure to each point of the sequence indicated by the indicating means and for measuring the pressure applied by said pressure algometer.

7. An algometry management system as recited in claim 6, wherein:

the pressure algometer comprises a patient-operated stop push-button, and means for holding a measurement of the pressure being applied to the point of the patient's body when the patient indicates that a threshold of pain has been reached by depressing the stop push-button;

said receiving means comprises means for receiving the held pressure measurement from the pressure algometer; and said storing means comprises means for storing the received, held pressure measurement in the file of the patient.

8. An algometry management system as recited in claim 7, wherein the pressure measurement held by the pressure algometer is in the form of an analog signal, said algometry management system further comprising an analog-to-digital converter for converting said analog signal into a pressure representative digital signal supplied to said receiving means.

9. An algometry management system comprising:

means for selecting points of a patient's body on which pain sensitivity measurements are to be made by an operator;

means for determining a sequence of the selected points;

means for indicating to the operator, according to said sequence, each selected point of the patient's body on which a pain sensitivity measurement is to be made;

means for receiving the pain sensitivity measurement made by the operator on each point of said sequence indicated by said indicating means;

means for storing the received pain sensitivity measurement of each point of said sequence in a file associated with the patient;

means for asking the patient for a subjective indication of an intensity of pain felt during each pain sensitivity measure; and patient-operated means for producing a signal representative of said subjective indication, wherein said receiving means comprises means for receiving said pain intensity subjective indication representative signal and said storing means comprises means for storing said pain intensity subjective indication representative signal in the file of the patient, said patient-operated means including;

(a) a visual analog scale;

(b) cursor means displaceable along the visual analog scale to produce the subjective indication of the intensity of pain the patient felt; and (c) means for converting a resulting position of the cursor means along the visual analog scale into said pain intensity subjective indication representative signal.

10. An algometry management system, comprising:

means for selecting points of a patient's body on which pain sensitivity measurements are to be made by an operator;

means for determining a sequence of the selected points;

means for indicating to the operator, according to said sequence, each selected point of the patient's body on which a pain sensitivity measurement is to be made;

means for receiving the pain sensitivity measurement made by the operator on each point of said sequence indicated by said indicating means;

means for storing the received pain sensitivity measurement of each point of said sequence in a file associated with the patient;

means for asking the patient for a subjective indication of a degree of discomfort felt during each pain sensitivity measure; and patient-operated means for producing a signal representative of said discomfort degree subjective indication, wherein said receiving means comprises means for receiving said discomfort degree subjective indication representative signal and said storing means comprises means for storing said discomfort degree subjective indication representative signal in the file of the patient, said patient-operated means including;

(a) a visual analog scale;

(b) cursor means displaceable along the visual analog scale to produce the subjective indication of the degree of discomfort the patient felt; and (c) means for converting a resulting position of the cursor means along the visual analog scale into a said discomfort degree subjective indication representative signal.

11. An algometry management system comprising:

means for selecting points of a patient's body on which pain sensitivity measurements are to be made by an operator;

means for determining a sequence of the selected points;

means for indicating to the operator, according to said sequence, each selected point of the patient's body on which a pain sensitivity measurement is to be made;

means for receiving the pain sensitivity measurement made by the operator on each point of said sequence indicated by said indicating means;

means for storing the received pain sensitivity measurement of each point of said sequence in a file associated with the patient; and a portable visual analog scale data collecting unit in which data about a patient is entered; and means for transferring data from said portable data collecting unit to said receiving means, wherein said receiving means includes means for receiving the transferred data, and said storing means includes means for storing the received, transferred data in a file of the patient whose data was entered in the portable data collecting unit.

12. An algometry management method, comprising the steps of:

selecting points of a patient's body on which pain sensitivity measurements are to be made by an operator;

determining a sequence of the selected points;

indicating to the operator, according to said sequence, each selected point of the patient's body on which a pain sensitivity measurement is to be made;

receiving the pain sensitivity measurement made by the operator on each point of said sequence indicated by said indicating means;

storing the received pain sensitivity measurement of each point of said sequence in a file associated with the patient;

asking the patient for a subjective indication of at least one sensation felt during each pain sensitivity measure; and producing a signal representative of said subjective indication, wherein said receiving step comprises receiving said subjective indication representative signal and said storing step comprises storing said subjective indication representative signal in the file of the patient, said signal producing step including the steps of;
(a) displacing a cursor means along a visual analog scale to produce said subjective indication; and
(b) converting a resulting position of the cursor means along the visual analog scale into said subjective indication representative signal.

13. An algometry management method as recited in claim 12, wherein said step of selecting points of a patient's body comprises:

displaying at least one representation of the patient's body; and marking on said at least one representation of the patient's body the selected points.

14. An algometry management method as recited in claim 13, wherein said step of selecting points of a patient's body comprises selecting bilateral points and marking said bilateral points on said at least one representation of the patient's body.

15. An algometry management method as recited in claim 12, wherein said step of determining a sequence of the selected points comprises producing a random sequence of the selected points.

16. An algometry management method as recited in claim 12, wherein said step of indicating to the operator, according to said sequence, each selected point of the patient's body comprises indicating one by one the points of the sequence on said at least one representation of the patient's body.

17. An algometry management method as recited in claim 12, further comprising the steps of:

applying pressure to each point of the sequence indicated by the indicating step;

measuring the pressure applied in said pressure applying a step; and holding a measurement of the pressure being applied to the point of the patient's body when the patient indicates that a threshold of pain has been reached, wherein said receiving step comprises receiving the held pressure measurement, and said storing step comprises storing the received, held pressure measurement in the file of the patient.

18. An algometry management system as recited in claim 12, wherein each pain sensitivity measurement comprises the step of applying pressure to a point of the patient's body indicated by said indicating step.

19. An algometry management method, comprising the steps of:

selecting points of a patient's body on which pain sensitivity measurements are to be made by an operator;

determining a sequence of the selected points;

indicating to the operator, according to said sequence, each selected point of the patient's body on which a pain sensitivity measurement is to be made;

receiving the pain sensitivity measurement made by the operator on each point of said sequence indicated by said indicating means;

storing the received pain sensitivity measurement of each point of said sequence in a file associated with the patient;

asking the patient for a subjective indication of an intensity of pain felt during each pain sensitivity measurement; and producing a signal representative of said pain intensity subjective indication, wherein said receiving step comprises receiving said intensity subjective indication representative signal and said storing step comprises storing said pain intensity subjective indication representative signal, said signal producing step includes the steps of;
(a) displacing a cursor means along a visual analog scale to produce said subjective indication of the intensity of pain the patient felt; and
(b) converting a resulting position of the cursor means along the visual analog scale into said pain intensity subjective indication representative signal.

20. An algometry management method, comprising the steps of:

selecting points of a patient's body on which pain sensitivity measurements are to be made by an operator;

determining a sequence of the selected points;

indicating to the operator, according to said sequence, each selected point of the patient's body on which a pain sensitivity measurement is to be made;

receiving the pain sensitivity measurement made by the operator on each point of said sequence indicated by said indicating means;

storing the received pain sensitivity measurement of each point of said sequence in a file associated with the patient; asking the patient for a subjective indication of a degree of discomfort felt during each pain sensitivity measurement; and producing a signal representative of said discomfort degree subjective indication, wherein said receiving step comprises receiving said discomfort degree subjective indication representative signal and said storing step comprises storing said discomfort degree subjective indication representative signal, said signal producing step including the steps of;
(a) displacing a cursor means along a visual analog scale to produce the subjective indication of the degree of discomfort the patient felt; and
(b) converting a resulting position of the cursor means along the visual analog scale into said discomfort degree subjective indication representative signal.

21. An algometry management system, comprising:

means for selecting points of a patient's body on which pain sensitivity measurements are to be made by an operator;

means for determining a sequence of the selected points;

means for indicating to the operator, according to said sequence, each selected point of the patient's body on which a pain sensitivity measure is to be made;

means for receiving the pain sensitivity measurement made by the operator on each point of said sequence indicated by said indicating means;

means for storing the received pain sensitivity measurement of each point of said sequence in a file associated with the patient;

means for asking to the patient for a subjective indication of a degree of discomfort felt during each pain sensitivity measurement; and patient-operated means for producing a signal representative of said discomfort degree subjective indication, wherein said receiving means comprises means for receiving said discomfort degree subjective indication representative signal and said storing means comprises means for storing said discomfort degree subjective indication representative signal in the file of the patient.

22. An algometry management method comprising the steps of:

selecting points of a patient's body on which pain sensitivity measurements are to be made by an operator;

determining a sequence of the selected points;

indicating to the operator, according to said sequence, each selected point of the patient's body on which a pain sensitivity measurement is to be made;

receiving the pain sensitivity measurement made by the operator on each point of said sequence indicated by said indicating means;

storing the received pain sensitivity measurement of each point of said sequence in a file associated with the patient;

asking the patient for a subjective indication of a degree of discomfort felt during each pain sensitivity measure; and producing a signal representative of said discomfort degree subjective indication, wherein said receiving step comprises receiving said discomfort degree subjective indication representative signal and said storing step comprises storing said discomfort degree subjective indication representative signal.

* * * * *